US012560528B2

(12) United States Patent
Galavotti et al.

(10) Patent No.: US 12,560,528 B2
(45) Date of Patent: Feb. 24, 2026

(54) METHODS AND DEVICES FOR MONITORING BLOOD

(71) Applicant: Sorin Group Italia S.r.l., Milan (IT)

(72) Inventors: Andrea Galavotti, Mirandola (IT);
Gabriele Tommasi, Cavezzo (IT);
Giampaolo Simonini, Reggio
nell'Emilia (IT); Marco Luppi,
Cavezzo (IT); Andrea Zaniboni, San
Martino Spino (IT); Paola Capriati,
Mirandola (IT)

(73) Assignee: Sorin Group Italia S.r.l., Milan (IT)

( * ) Notice: Subject to any disclaimer, the term of this
patent is extended or adjusted under 35
U.S.C. 154(b) by 0 days.

(21) Appl. No.: 18/643,074

(22) Filed: Apr. 23, 2024

(65) Prior Publication Data

US 2024/0272065 A1      Aug. 15, 2024

Related U.S. Application Data

(63) Continuation of application No. 17/545,620, filed on
Dec. 8, 2021, now Pat. No. 11,994,460, which is a
(Continued)

(51) Int. Cl.
*G01N 21/03*          (2006.01)
*A61B 5/1455*        (2006.01)
(Continued)

(52) U.S. Cl.
CPC ..... *G01N 21/0303* (2013.01); *A61B 5/14557*
(2013.01); *G01N 21/645* (2013.01);
(Continued)

(58) Field of Classification Search
CPC ............. G01N 21/0303; G01N 21/645; G01N
2021/0367; G01N 2021/6432;
(Continued)

(56) References Cited

U.S. PATENT DOCUMENTS

| | | | |
|---|---|---|---|
| 3,868,707 A | 2/1975 | Bahnsen et al. | |
| 3,936,196 A | 2/1976 | Wickersheim | |
| | (Continued) | | |

FOREIGN PATENT DOCUMENTS

| | | |
|---|---|---|
| CN | 205430252 U | 8/2016 |
| CN | 107582070 A | 1/2018 |
| | (Continued) | |

OTHER PUBLICATIONS

International Search Report and Written Opinion received for
International Application No. PCT/IB2016/053520, mailed on Apr.
4, 2017, 15 pages.

*Primary Examiner* — Mohamed K Amara
(74) *Attorney, Agent, or Firm* — Seager, Tufte &
Wickhem LLP

(57) ABSTRACT

A system includes a cuvette including a cuvette body
forming a substantially planar exterior surface and having a
sensor window defined within the substantially planar exte-
rior surface. The cuvette further includes a probe retention
structure extending from the cuvette body. The system
includes a probe with a probe body and a protrusion that is
removably coupled to the probe retention structure.

18 Claims, 7 Drawing Sheets

Related U.S. Application Data continuation of application No. 16/309,065, filed as application No. PCT/IB2016/053520 on Jun. 15, 2016, now Pat. No. 11,226,282.

(51) Int. Cl.
G01N 21/64 (2006.01)
A61B 5/15 (2006.01)

(52) U.S. Cl.
CPC ..... *A61B 5/150992* (2013.01); *G01N 2021/0367* (2013.01); *G01N 2021/6432* (2013.01); *G01N 2021/6482* (2013.01)

(58) Field of Classification Search
CPC ........ G01N 2021/6482; A61B 5/14557; A61B 5/150992
See application file for complete search history.

(56) References Cited

U.S. PATENT DOCUMENTS

| | | | |
|---|---|---|---|
| 4,444,498 A | 4/1984 | Heinemann | |
| 4,447,150 A | 5/1984 | Heinemann | |
| 4,640,820 A | 2/1987 | Cooper | |
| 4,745,279 A | 5/1988 | Karkar et al. | |
| 5,289,255 A * | 2/1994 | Mullin | G01N 21/05 356/41 |
| 5,304,492 A | 4/1994 | Klinkhammer | |
| 5,314,723 A | 5/1994 | Dutta et al. | |
| 5,335,658 A | 8/1994 | Bedingham | |
| 5,339,375 A * | 8/1994 | Kerns | G01N 21/274 385/53 |
| 5,351,686 A | 10/1994 | Steuer et al. | |
| 5,463,466 A | 10/1995 | Svendsen | |
| 5,628,310 A | 5/1997 | Rao et al. | |
| 5,641,458 A | 6/1997 | Shockley, Jr. et al. | |
| D409,750 S | 5/1999 | Hacker | |
| D410,086 S | 5/1999 | Hacker et al. | |
| 5,944,660 A | 8/1999 | Kimball et al. | |
| 6,009,339 A * | 12/1999 | Bentsen | A61B 5/14557 600/322 |
| 6,101,406 A | 8/2000 | Hacker et al. | |
| 6,143,247 A | 11/2000 | Sheppard, Jr. et al. | |
| 6,144,444 A | 11/2000 | Haworth et al. | |
| 6,184,526 B1 | 2/2001 | Kohama et al. | |
| 7,468,033 B2 | 12/2008 | Van Antwerp et al. | |
| 7,481,787 B2 | 1/2009 | Gable et al. | |
| 8,743,354 B2 | 6/2014 | Barrett et al. | |
| 8,842,274 B2 | 9/2014 | Harnack et al. | |
| 8,888,730 B2 * | 11/2014 | Rossi | A61M 1/3666 604/4.01 |
| 9,370,324 B2 | 6/2016 | Barrett et al. | |
| 9,801,993 B2 * | 10/2017 | Barrett | A61M 1/3609 |
| 10,471,201 B2 * | 11/2019 | Barrett | A61M 1/36 |
| 2001/0036039 A1 | 11/2001 | Yamamoto et al. | |
| 2002/0005352 A1 | 1/2002 | Offenbacher | |
| 2002/0051979 A1 | 5/2002 | Chen et al. | |
| 2003/0014094 A1 * | 1/2003 | Hammack | A61F 7/12 607/105 |
| 2003/0190262 A1 | 10/2003 | Blazewicz et al. | |
| 2004/0001618 A1 | 1/2004 | Johnson et al. | |
| 2004/0249593 A1 | 12/2004 | Dunleavy et al. | |
| 2005/0035983 A1 | 2/2005 | Cruchon-Dupeyrat et al. | |
| 2005/0215946 A1 * | 9/2005 | Hansmann | A61B 8/0808 606/41 |
| 2006/0029979 A1 | 2/2006 | Bai et al. | |
| 2007/0073160 A1 | 3/2007 | Imam | |
| 2007/0230859 A1 | 10/2007 | Bock et al. | |
| 2009/0216097 A1 | 8/2009 | Wilson et al. | |
| 2009/0236504 A1 * | 9/2009 | Yamaguchi | G09G 3/3406 257/431 |
| 2011/0009720 A1 * | 1/2011 | Kunjan | A61B 5/15003 600/581 |
| 2011/0317171 A1 | 12/2011 | Emtman et al. | |
| 2012/0029329 A1 | 2/2012 | Braig et al. | |
| 2012/0218541 A1 | 8/2012 | Barrett et al. | |
| 2013/0171614 A1 | 7/2013 | Taccini | |
| 2013/0203172 A1 | 8/2013 | Wex et al. | |
| 2015/0136961 A1 | 5/2015 | Eddy et al. | |
| 2015/0263238 A1 * | 9/2015 | Fujihara | B81B 7/0067 428/137 |
| 2016/0370172 A1 | 12/2016 | Christoph et al. | |
| 2017/0103440 A1 * | 4/2017 | Xing | H04W 12/06 |
| 2021/0196881 A1 | 7/2021 | Walls et al. | |
| 2021/0308354 A1 * | 10/2021 | Kotanko | A61M 1/3661 |
| 2022/0175416 A1 | 6/2022 | Ebnet | |
| 2025/0134463 A1 * | 5/2025 | Chae | A61B 5/150969 |

FOREIGN PATENT DOCUMENTS

| | | |
|---|---|---|
| EP | 0510377 A2 | 10/1992 |
| EP | 2801852 A1 | 11/2014 |
| JP | H0414669 A | 1/1992 |
| JP | H04131770 U | 12/1992 |
| JP | H0835927 A | 2/1996 |
| JP | H09500721 A | 1/1997 |
| JP | 2001513675 A | 9/2001 |
| JP | 2008536140 A | 9/2008 |
| WO | 9427495 A1 | 12/1994 |
| WO | 9837801 A1 | 9/1998 |
| WO | 2006109282 A1 | 10/2006 |
| WO | 2013006716 A1 | 1/2013 |
| WO | 2020006549 A1 | 1/2020 |

* cited by examiner

METHODS AND DEVICES FOR MONITORING BLOOD

CROSS REFERENCE TO RELATED APPLICATIONS

This application is a continuation of U.S. patent application Ser. No. 17/545,620, filed Dec. 8, 2021, which is a continuation of U.S. patent application Ser. No. 16/309,065, filed Dec. 11, 2018, which is a National Stage Application of PCT/IB2016/053520, filed Jun. 15, 2016, the entirety of which are incorporated herein by reference.

TECHNICAL FIELD

The present disclosure relates generally to blood monitoring equipment used during cardiac surgery, for example.

BACKGROUND

During surgery, a patient's vascular system may be connected to an extracorporeal circuit that temporarily replaces the function of the heart and lungs. An extracorporeal blood circuit (ECC) may include, among other features, a pump to replace heart functions, and an oxygenation device to replace lung functions. The present disclosure relates to blood monitoring systems, methods, and devices that may be used as part as an extracorporeal blood circuit.

SUMMARY

In Example 1, a system includes a cuvette including a cuvette body forming a substantially planar exterior surface and having a sensor window defined within the substantially planar exterior surface. The cuvette further includes a probe retention structure extending from the cuvette body. The system includes a probe with a probe body and a protrusion that is removably coupled to the probe retention structure.

In Example 2, the system of Example 1, wherein the protrusion is coupled to a spring-loaded assembly at least partially positioned within the probe body.

In Example 3, the system of any of Examples 1-2, wherein the cuvette further include at least one pin extending from the cuvette body, the at least one pin mechanically coupled to the probe.

In Example 4, the system of any of Examples 1-3, wherein the probe further includes sensors positioned in alignment with the sensor window.

In Example 5, the system of Example 4, wherein the sensors include an optical sensor.

In Example 6, the system of any of Examples 1-5, wherein the probe retention structure forms an indent with at least a portion of the protrusion extending therein.

In Example 7, the system of any of Examples 1-6, wherein the probe retention structure forms an aperture with at least a portion of the protrusion extending therein.

In Example 8, the system of Example 1, wherein the protrusion is integrally formed with the probe body.

In Example 9, the system of any of Examples 1-8, wherein the probe retention structure is flexible.

In Example 10, the system of any of Examples 1-9, wherein the protrusion is deformable.

In Example 11, a cuvette includes a cuvette body including a sensor window frame, a sensor window positioned in the sensor window frame, and a window retainer mechanically coupling the sensor window to the cuvette body.

In Example 12, the cuvette of Example 11, wherein the cuvette body forms at least two teeth mechanically coupled to the window retainer.

In Example 13, the cuvette of any of Examples 11-12, further including an O-ring positioned between the sensor window and the sensor window frame.

In Example 14, the cuvette of any of Examples 11-13, wherein the sensor window includes a fluorescent coating.

In Example 15, the cuvette of any of Examples 11-14, wherein the sensor window comprises polyvinilydenefluoride.

In Example 16, the cuvette of any of Examples 11-15, wherein the sensor window has a biocompatible film coating on a surface facing a central bore formed by the cuvette body.

In Example 17, the cuvette of any of Examples 1-16, wherein the cuvette body includes an exterior surface that is substantially planar, and wherein the single sensor window frame is defined in the substantially planar surface.

In Example 18, the cuvette of any of Examples 1-17, wherein the probe retention structure is positioned near an end of the cuvette body.

In Example 19, the cuvette of Example 18, wherein the probe retention structure comprises an aperture.

In Example 20, a system includes a cuvette including a cuvette body having a first cuvette end and a second cuvette end. The cuvette further includes a window frame positioned between the first and second cuvette ends, a window positioned within the window frame, a first probe retention structure positioned near the first cuvette end, and a second probe retention structure extending from the cuvette body and positioned near the second cuvette end. The system further includes a probe having a probe body, a first probe end, and a second probe end. The probe further includes a first cuvette engaging structure near the first probe end, capable of engaging the first probe retention structure, and a second cuvette engaging structure near the second probe end, capable of removably engaging the second probe retention structure.

In Example 21, the system of Example 20, further comprising at least one structure selected from: a first probe retention structure comprising at least one pin, a second probe retention structure comprising at least one aperture, a first cuvette engaging structure comprising at least one bearing surface, and a second cuvette engaging structure comprising at least one protrusion.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
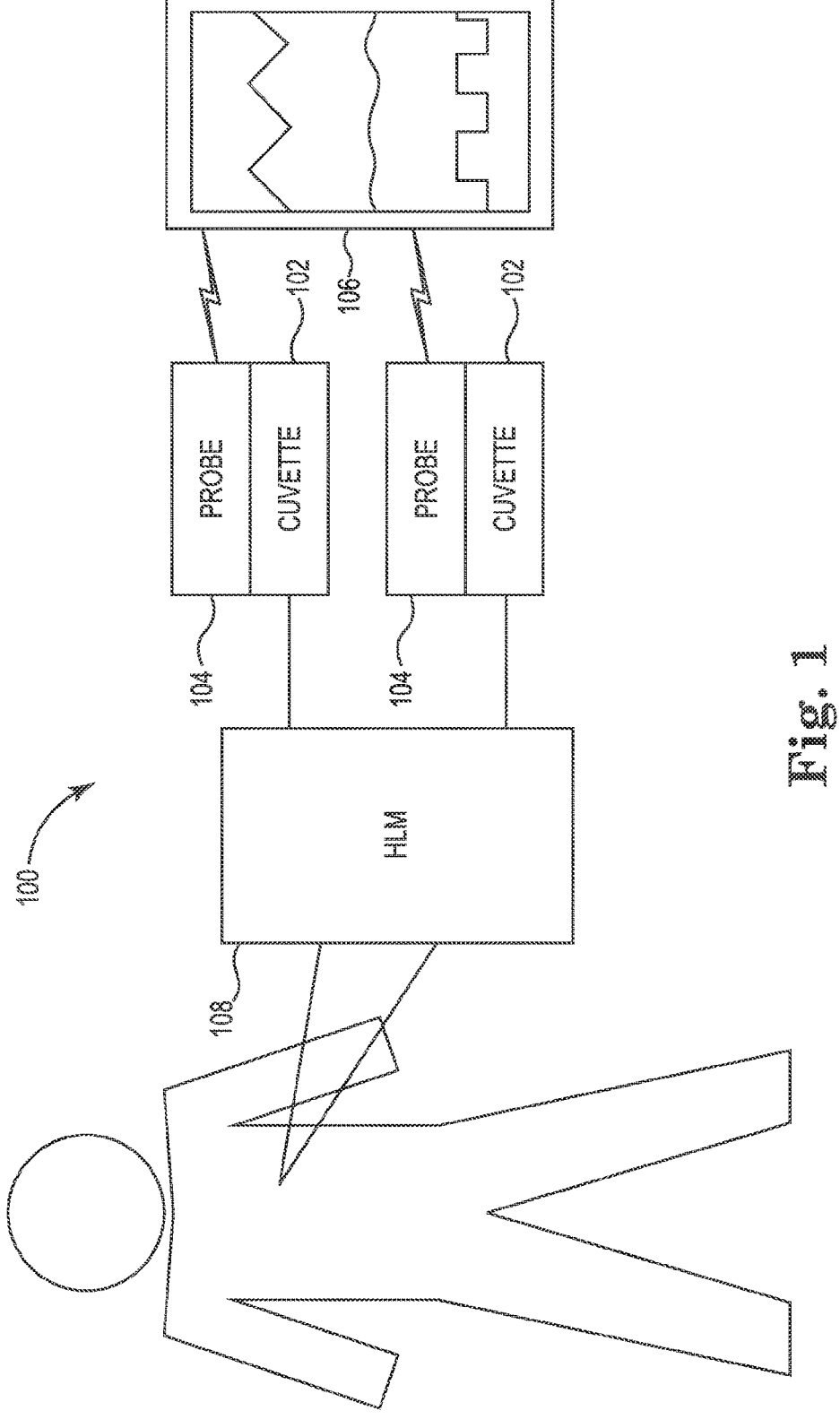
FIG. 1 shows a schematic illustration of a blood monitoring system in accordance with certain embodiments of the present disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic illustration of a blood monitoring system 100 incorporated in an extracorporeal blood circuit (ECC). During surgery, a patient's blood can be directed through an ECC, which may feature a heart-lung machine that receives blood and returns blood and other fluids to a patient, an oxygenator, and a reservoir among other equipment (not shown in FIG. 1). The ECC may also include blood monitoring equipment for measuring one or more parameters or properties of blood at one or more locations within the ECC. Blood monitoring equipment may include cuvettes 102 through which blood flows, probes 104 coupled to the cuvettes, and a monitor 106 in communication with the probes. A first cuvette/probe assembly can be positioned on an arterial blood line (e.g., to measure blood parameters after oxygenation before it is returned to the patient) while a second cuvette/probe assembly can be positioned on a venous blood line (e.g., to measure blood parameters for venous blood before treatment in the ECC). Cuvettes 102 are single-use cuvettes and disposed after one use. As will be discussed in further detail below, a probe 104 for providing a blood parameter signal may be reusable (e.g., attachable and detachable from a cuvette 102 such that the probe can be reused).

Blood monitoring equipment may include various sensing elements for measuring properties of venous and/or arterial blood. In some embodiments, it may be desirable to measure hematocrit, oxygen saturation, and temperature, among other parameters of venous blood. Such measurements may be made using a variety of sensor types, including electronic, chemical, optical, etc. For example, hematocrit measurements can be carried out by utilizing LEDs that emit light in a range or set of wavelengths into blood. Blood scatters the emitted light, and characteristics of the scattering can be sensed by an optical sensor and used to provide signals from which the hematocrit level of the blood may be determined. Oxygen saturation also can be measured using an optical sensor. Blood temperature can be measured using infrared sensors, which can measure temperature without contacting blood. In some embodiments, it may be desirable to measure oxygen partial pressure and temperature, among other parameters of arterial blood. Measurements of oxygen partial pressure can be carried out using fluorescence or oxygen quenching, as will described in greater detail below. Like with venous blood, temperature of arterial blood can be measured using infrared sensors. It should be appreciated that sensors providing a wide variation in both signal type (e.g., electronic, optical) and construction may be used in embodiments of the present disclosure.

Referring again to FIG. 1, probes 104 can communicate with and direct measurements to the monitor 106, which may be integrated with a heart-lung machine (HLM) 108 or to a stand-alone device that can be coupled to a machine like a heart-lung machine. While the HLM 108 is shown schematically between the patient and the cuvettes 102 and probes 104, as described in more detail herein, the probes and cuvettes may be placed at various locations along the blood circuit, including at locations between the HLM 108 and the patient. For example, one cuvette 102 and probe 104 may be placed in a venous blood line to measure properties of venous blood, and a second cuvette and probe may be placed in an arterial line to measure properties of arterial blood.

In one embodiment, the monitor 106 can display measurements taken from various sensors associated with one or more cuvette/probe assemblies. Monitor 106 may also display measurements from other monitoring devices. For example, the monitor 106 may display patient, surgical, and blood measurements and calculated parameters such as temperature, hematocrit, hemoglobin, oxygen delivery, carbon dioxide production, body surface area, and ventilation, among others.

Figure 2A:
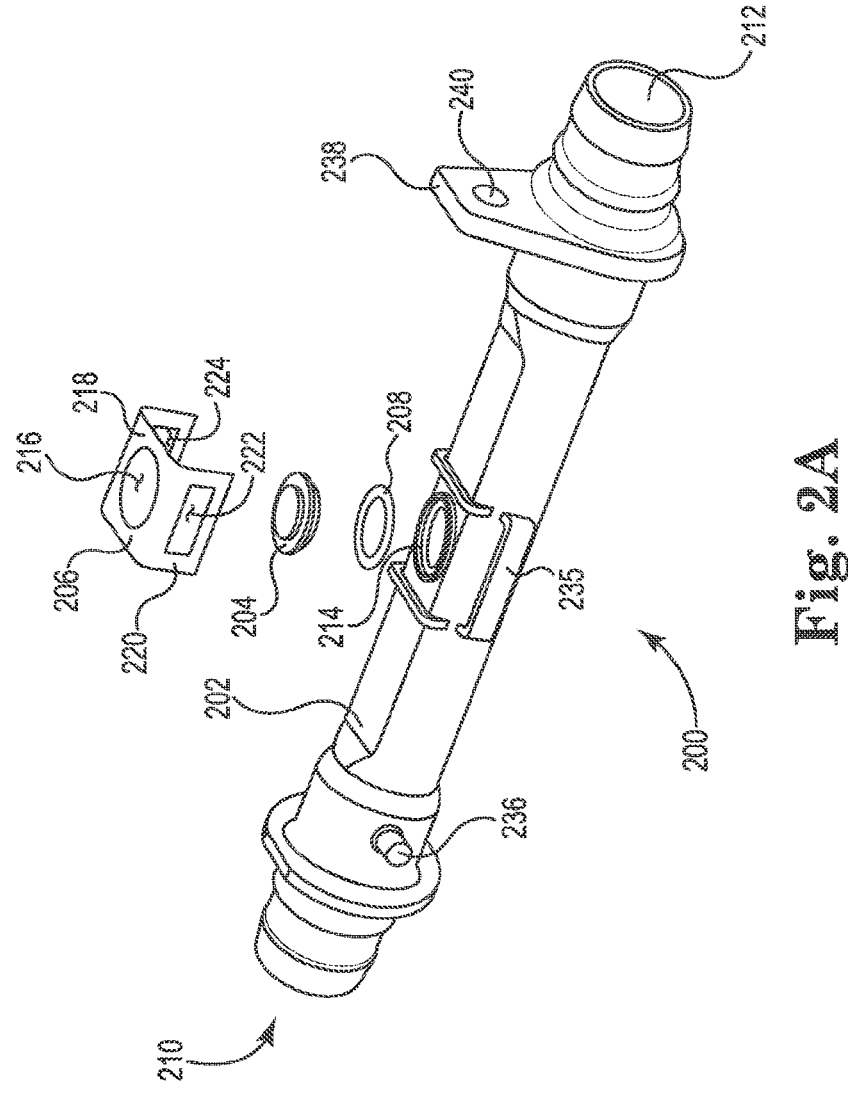
FIG. 2A shows an exploded perspective view of a cuvette in accordance with certain embodiments of the present disclosure.

FIG. 2A shows an exploded view of a cuvette 200 having a cuvette body 202, sensor window 204, window retainer 206, and an O-ring 208. The cuvette body 202 has a hollow inner portion with a first end 210 and a second end 212 for allowing blood flow through a central bore of the cuvette. An exterior surface of the cuvette body 202 is generally cylinder-shaped but includes a planar or substantially planar surface on a portion of the body to which a probe may be coupled. The cuvette body 202 defines at least one sensor window, such as single sensor window frame 214 in the form of a aperture in a portion of the cuvette body. When assembled, the sensor window 204 is positioned within single window frame 214 and permits visual and/or sensor access to blood within the central bore of the cuvette, while preventing blood leakage or flow through the aperture.

In one embodiment, the window 204 may be made of an optically transmissive polymer such as polyvinilydenefluoride (PVDF) and may be provided with a fluorescent coating or paint. The fluorescent coating can be of a kind sensitive to blood oxygen partial pressure such that the paint changes colors or shades in response to varying oxygen partial pressures. In some embodiments, the entire window may be made of an optically transmissive, biocompatible polymer and no additional coating may be necessary for biocompatibility. The window 204 and window frame 214 in FIG. 2A as having a circular shape, but it will be appreciated that other shapes may readily be employed. In one embodiment, the cuvette 200 of FIGS. 2A and 2B may be used as an arterial line cuvette.

Figure 2B:
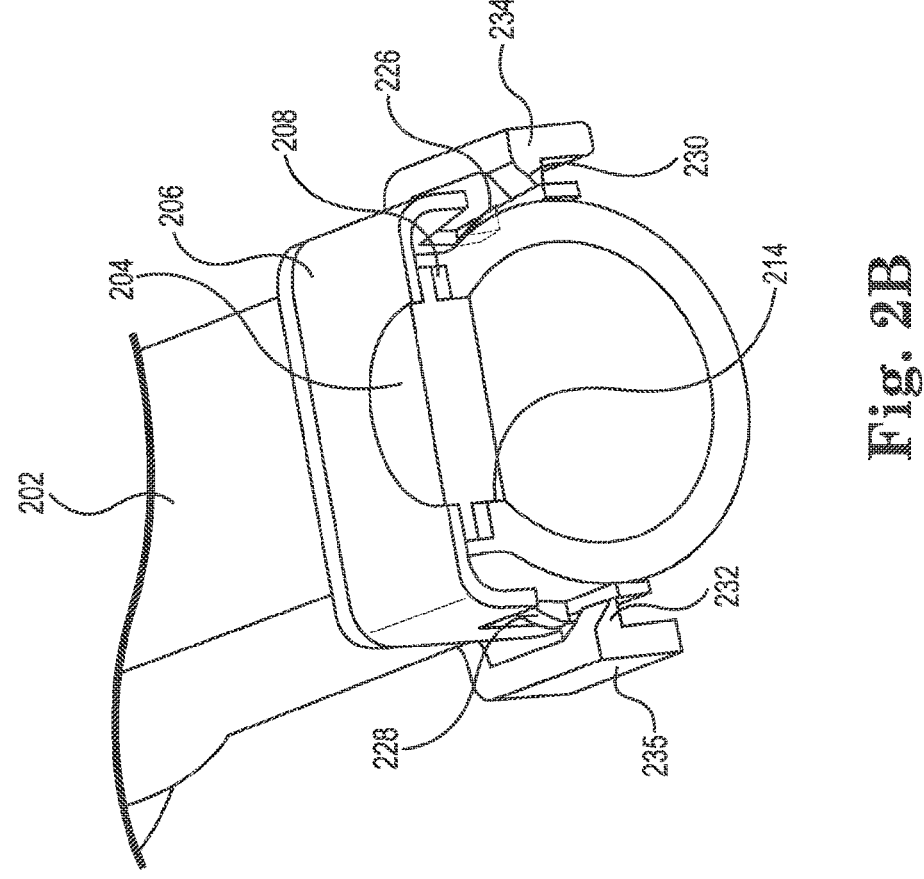
FIG. 2B shows a cross-sectioned perspective view of a cuvette in accordance with certain embodiments of the present disclosure

As shown in FIG. 2B, which is a cross-sectioned view of an assembled cuvette of FIG. 2A, the window 204 is secured to the cuvette body 202 by a retainer 206. The window 204 is shown as having a thickness that extends into the aperture of window frame 214. In some embodiments, a sealing element such as O-ring 208 is positioned over the surface of window frame 214 that extends radially from a central portion of the window. The O-ring 208 seals the window frame 214 such that blood will not leak through the frame.

A window retainer 206 shown in FIG. 2A is U-shaped and defines various apertures. The circular aperture 216 formed in a surface 218 of the window retainer 206 is configured to be aligned with the window 204 to permit optical and/or sensor access to blood in the cuvette. Although the aperture 216 is shown as being circular shaped, other shapes are contemplated by Applicants. Legs 220 extend generally perpendicular to the surface 218 and form apertures 222, 224 that assist with coupling the retainer 206 to the cuvette body 202.

Shown in FIG. 2B are sets of teeth 226-232 that, when assembled, are formed to engage window retainer apertures 222, 224 to couple the window retainer 206 and cuvette body 202. First teeth 226, 228 are positioned on opposite sides of the cuvette body 202. These teeth extend directly from the cuvette body 202 and are shown as being triangular shapes that protrude from the body, but it will be appreciated that other shapes may readily be employed. Also extending from the body are one or more L- or U-shaped components 234, 235 having teeth 230, 232 that protrude towards the cuvette body 202 and are also triangular in shape, although other shapes may be used. As shown in FIG. 2B, the window retainer 206 slips over the teeth 226-232 such that the teeth extend into the retainer's apertures 222, 224 to secure the retainer 206 (and window 204 and O-ring 208) to the cuvette body 202. The retainer 206 may be formed of a variety of suitable materials, such as metals or plastics.

Referring again to FIG. 2A, a first probe retention structure, such as pins 236 shown as extending from the cuvette body 202 on opposite sides of the body near the inlet 210, may be provided to assist with mechanically coupling a probe to the cuvette. Also extending from the body is a second probe retention structure, such as flange 238, which may also help to mechanically couple a probe to the cuvette 200. Flange 238 extends radially from a tube-like portion of the cuvette body near the outlet 212. Although the first probe retention structure (e.g., pins 236) is described as being positioned near the inlet 210 and the second probe retention structure (e.g., flange 238) is described as being positioned near the outlet 212, the position of the probe retention structures can be reversed or altered. In the embodiment of FIG. 2A, the second probe retention structure includes an aperture 240 or similar feature into which a portion of a probe may extend to assist with mechanically coupling a probe to the cuvette 200. As will be described in more detail below, the first and second probe retention structures 236 and 238 are positioned relative to each other such that, when a probe is coupled to the cuvette 200, air does not develop between the cuvette and probe and interfere with blood parameter measurements.

Figure 3A:
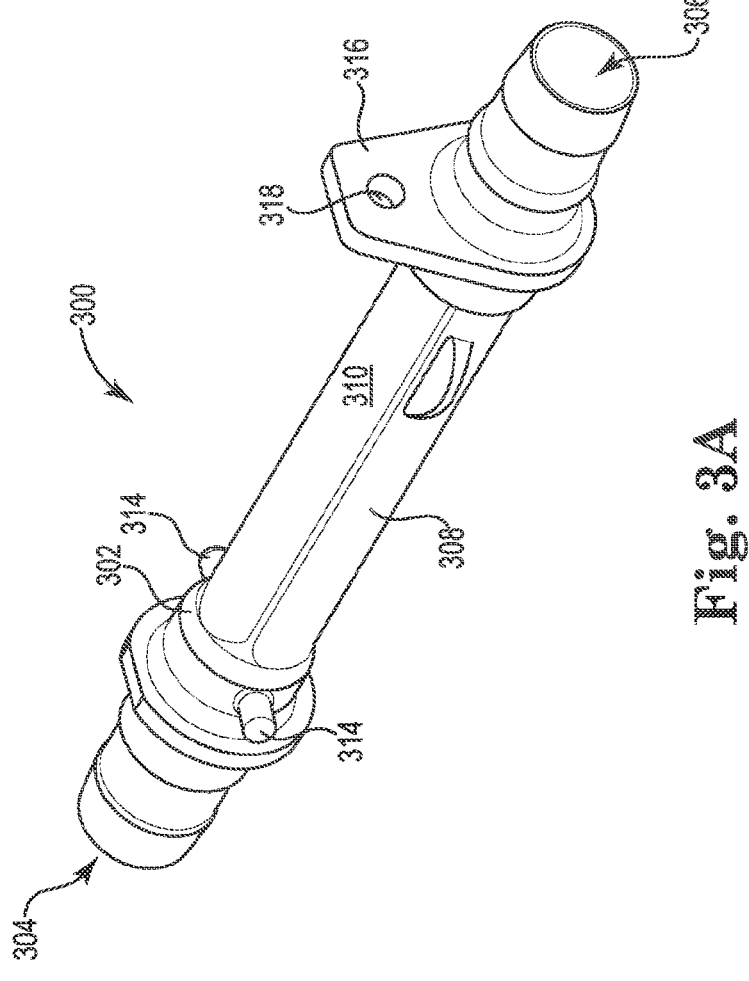
FIG. 3A shows a perspective view of a cuvette in accordance with certain embodiments of the present disclosure.
Figure 3B:
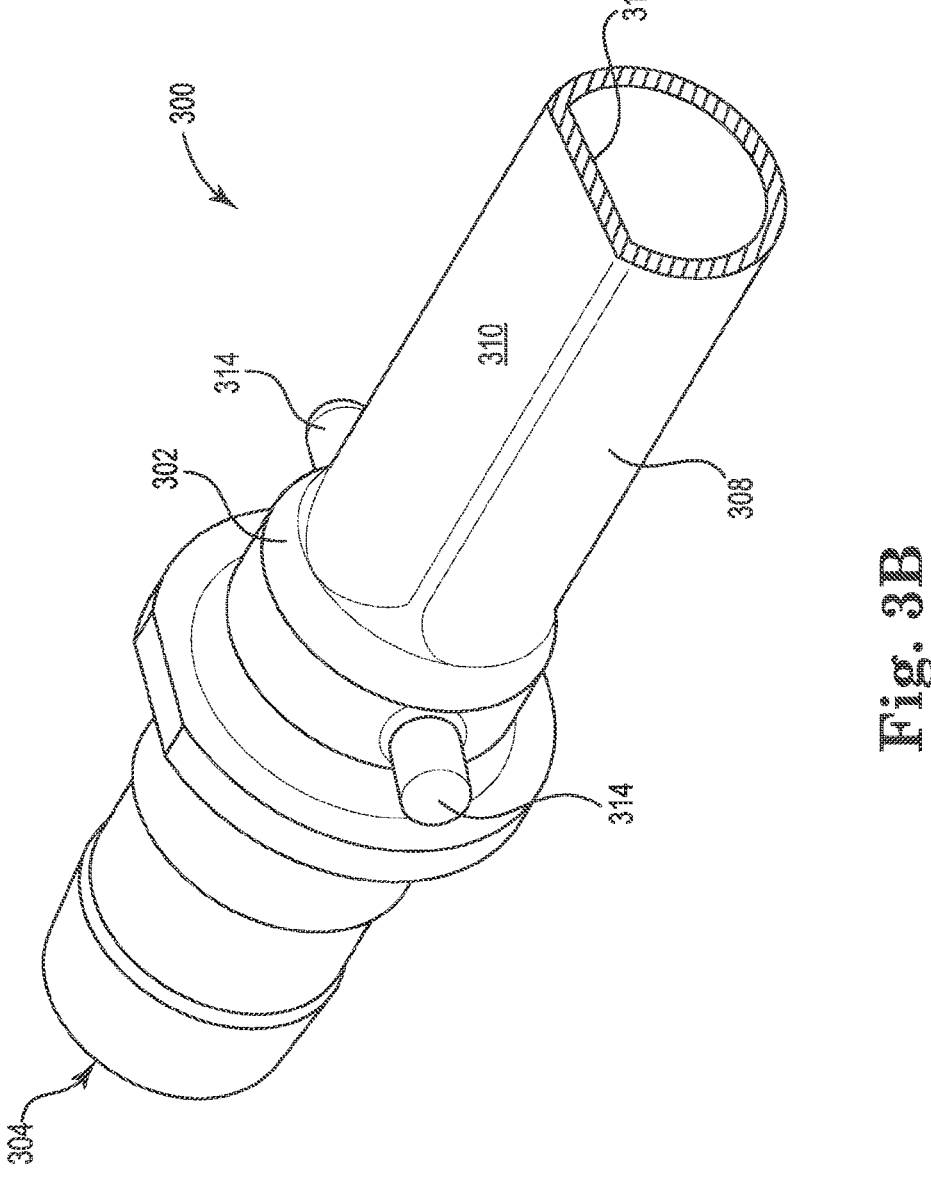
FIG. 3B shows a cross-sectioned perspective view of a cuvette in accordance with certain embodiments of the present disclosure.

FIG. 3A shows a perspective view of a cuvette 300, and FIG. 3B shows a sectional perspective view of the cuvette 300. The cuvette 300 shown in FIGS. 3A and 3B may be suitable for use as a venous cuvette. The cuvette 300 has a cuvette body 302 with a hollow inner portion with a first end 304 and a second end 306 for allowing blood flow through a central bore of the cuvette. An exterior surface of the cuvette body 308 is primarily cylinder-shaped but includes a flat or substantially flat surface 310 on a portion of the body on which a probe may rest. As shown in FIG. 3B, the inner portion includes a flat surface 312 that is substantially parallel to the flat surface 310. Because a cuvette within a venous blood circuit may not need to measure oxygen partial pressures, in some embodiments the cuvette 300 does not feature a window and window frame like those featured in FIGS. 2A and 2B. The cuvette 300 includes a first probe retention structure, such as retaining pins 314 extending from the cuvette body 302 on opposite sides. The pins 314 assist with mechanically coupling a probe to the cuvette.

Also extending from the body is a second probe retention structure, such as flange 316 extending from a portion of the cuvette body 302. The flange 316 defines an aperture 318 or similar feature into which a portion of a probe may extend to assist with mechanically coupling, e.g., a venous probe to the cuvette 300.

Figures 4, 5:
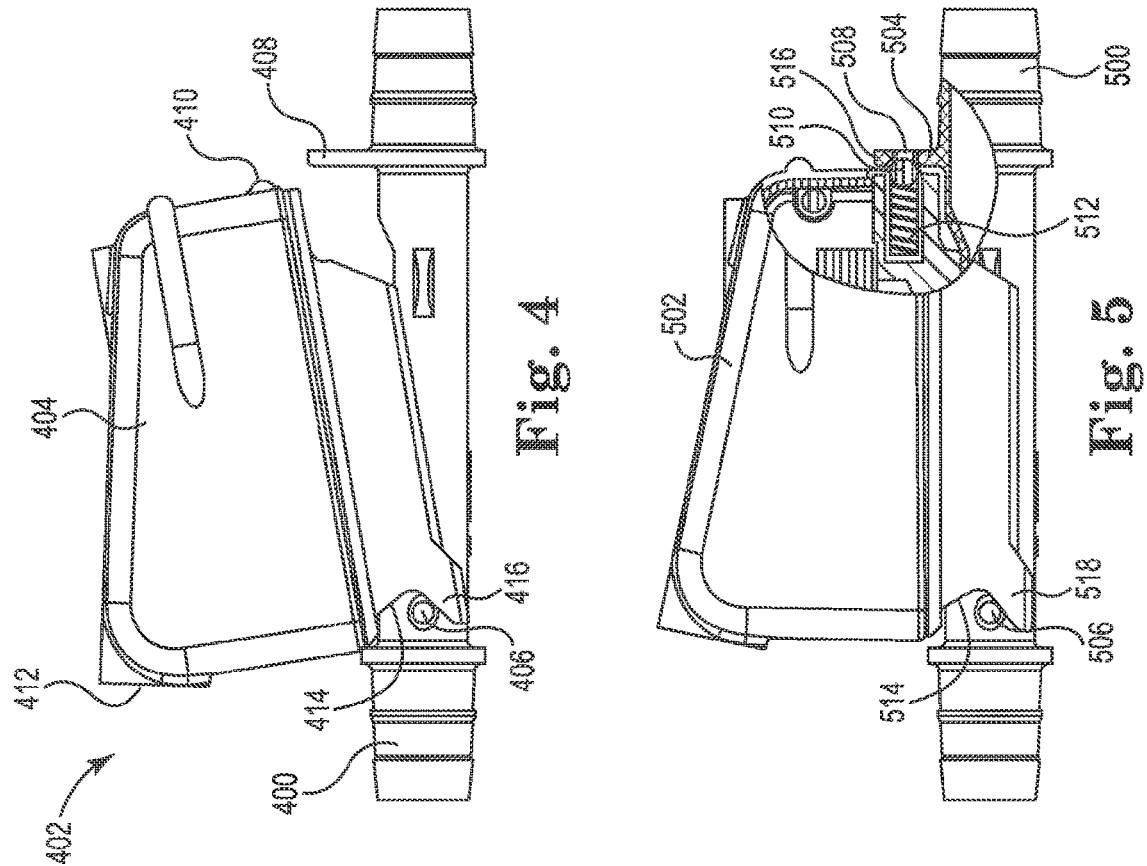
FIG. 4 shows a perspective view of a cuvette and probe in accordance with certain embodiments of the present disclosure.
FIG. 5 shows partial section view of a cuvette and probe assembly in accordance with certain embodiments of the present disclosure.

FIG. 4 shows a cuvette 400 and probe 402 with a probe body 404 partially coupled together. The cuvette 400 includes a first probe retention structure comprising pins 406 that mechanically couple the cuvette 400 to a first cuvette engaging structure 416 of the probe 402. The first cuvette engaging structure 416 may include a bearing surface 414, which may comprise a portion of a U-shaped channel as shown in FIG. 4, to enable the probe 402 to pivotally contact the first probe retention structure (e.g., pins 406) on cuvette 400. The cuvette 400 also includes a second retention structure that includes a flange 408 that extends from the cuvette 400. The flange 408 may include an aperture, indent, or the like to receive a second cuvette engaging structure such as boss or protrusion 410 extending from the probe 402. The first and second probe retention structures 406 and 408 assist with mechanically coupling the cuvette 400 to corresponding first and second cuvette engaging structures 416 and 410 on the probe 402.

The probe 402 may include various sensors, components, and related circuitry for monitoring blood as described above. For example, the probe 402 may include one or more of LEDs, optical sensors, and infrared sensors. In some embodiments, the probe includes an optical sensor that detects color changes of a window coupled to the cuvette 400 and covered with fluorescent coating or paint, which may be sensitive to blood oxygen partial pressure and change colors or shades in response to varying oxygen partial pressures. The probe 402 includes a communication port 412 that can communicatively couple (e.g., electrically or by wireless connection) the probe 402 and a monitor and/or processing equipment, for example.

FIG. 5 shows a partial section view of a cuvette 500 and probe 502 coupled together. The cuvette 500 includes a first probe retention structure that may include a set of pins 506 extending from the cuvette 500, as well as a second probe retention structure (e.g., flange 504) that includes an aperture 508 into which a portion of a probe's second cuvette engaging structure (e.g., boss or protrusion 510) extends. The protrusion 510 is shown as a sphere partially positioned within the probe 502, but it will be appreciated that other shapes may be used. The protrusion 510 is coupled to a spring assembly 512 positioned within the probe 502 that is configured to provide a spring force against the protrusion 510 biasing the protrusion to engage the second retention structure (e.g., aperture 508 in flange 504) on cuvette 500.

A first cuvette engaging structure 518 includes a bearing surface 514 to allow probe to engage first probe retention structure (e.g., pins 506) on cuvette 500. As the probe 502 is pivoted on bearing surface 514 around pins 506, the protrusion 510 contacts a portion 516 of the second probe retention structure 504 and compresses the spring assembly 512 such that the protrusion 510 recesses, at least partially, into the probe 502. Once the protrusion 510 aligns with the aperture 508, the spring assembly 512 decompresses and biases the protrusion 510 into the aperture 508 to couple the cuvette 500 and probe 502. In other embodiments, the second probe retention structure (e.g., flange 504) on the cuvette 500 may comprise other features, such as an indent rather than an aperture, to facilitate engagement with the second cuvette engaging structure on probe 502. The spring assembly 512 provides a sufficient spring force to maintain coupling between the probe 502 and cuvette 500 when engaged but also permits the probe 502 to disengage when desired. The probe 502 and its features, first probe retention structure (e.g., pins 506) and its features, and second prove retention structure (e.g., flange 504) are positioned relative to each other such that, when the probe 502 is coupled to the cuvette 500, air does not interfere with blood parameter measurements, which could cause inaccurate blood parameter measurements.

Figure 6:
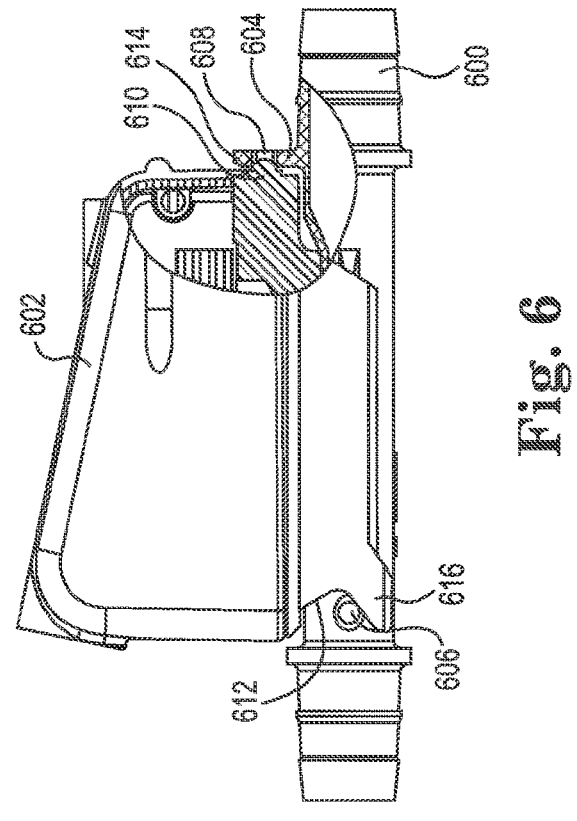
FIG. 6 shows partial section view of a cuvette and probe assembly in accordance with certain embodiments of the present disclosure.

FIG. 6 shows a cuvette 600 and a probe 602 coupled together. The cuvette 600 includes a first probe retention structure comprising a set of pins 606 and a second probe retention structure including a flange 604 extending from the cuvette 600. The second probe retention structure 604 includes an aperture 608 in which a portion of a probe's second cuvette engaging structure extends. The second cuvette engaging structure is depicted in FIG. 6 as a boss or protrusion 610, but other structures can be employed. A first cuvette engaging structure 616 including a bearing surface 612 is provided on probe 602 to pivotally engage pins 606 that comprise the cuvette's first probe retention structure to assist in coupling cuvette 600 and probe 602. The protrusion 610 shown in FIG. 6 is not coupled to a spring assembly and therefore may not be designed to move in and out of the probe 602. In certain embodiments, the probe 602 may be coupled to the cuvette 600 by pivoting probe 602 at the bearing surface 612 against the cuvette's pins 606 until the protrusion 610 engages the aperture 608. In the embodiment of FIG. 6, the second probe retention structure 604 has a degree of flexibility such that when the protrusion 610 contacts a portion 614 of the second probe retention structure, the exerted force flexes the second probe retention structure 604 to permit the protrusion 610 to move into aperture 608. As shown in FIG. 6, the portion 614 of the second probe retention structure 604 includes a slanted surface to provide camming action against the probe's second cuvette engaging structure (e.g., protrusion 610) to assist with sliding the protrusion 610 along the portion 614 towards the aperture 608. In some embodiments, the boss or protrusion 610 itself (or at least part of the boss or protrusion) has a degree of flexibility and may be temporarily deformed as the boss or protrusion moves along the retaining structure towards the aperture 608. Once the deformable boss or protrusion 610 is aligned with the aperture 608, the protrusion 610 can revert to its original shape and extend, at least partially, into the aperture 608 to mechanically couple the cuvette 600 and probe 602. In some embodiments, a cuvette may include a boss, protrusion, or similar structure that extends into an indent, aperture, or similar feature formed by a probe. Like embodiments described above, a cuvette's second probe retention structure (e.g., flange 604) may have a degree of flexibility to permit the structure to flex as the probe's second cuvette engaging structure (e.g., protrusion 610) slides into the indent or aperture to couple the cuvette and probe together. Alternatively, or in addition, a portion of the probe may be flexible to permit the boss or protrusion to slide and then extend into the indent or aperture.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method of monitoring blood in an extracorporeal blood circuit, comprising:

directing blood through a central bore of a cuvette, the cuvette comprising a cuvette body defining a wall having an aperture extending therethrough and a sensor window formed separately from and thereafter disposed across the sensor window of the cuvette body with an inner surface of the sensor window facing the central bore, wherein the blood directed through the central bore directly contacts the inner surface of the sensor window;

monitoring blood passing through the central bore via the sensor window using a probe disposed outside of the cuvette.

2. The method of claim 1, wherein the sensor window prevents blood flow through the aperture.

3. The method of claim 1, wherein the probe is releasably attachable to the cuvette.

4. The method of claim 1, wherein the sensor window comprises a biocompatible film coating on the inner surface facing the central bore.

5. The method of claim 1, wherein the sensor window comprises a fluorescent coating sensitive to blood oxygen partial pressures.

6. The method of claim 5, wherein the probe comprises an optical sensor positionable in alignment with the sensor window.

7. The method of claim 5, wherein the fluorescent coating is disposed in contact with blood passing through the central bore.

8. The method of claim 1, wherein the sensor window is formed from an optically transmissive polymer.

9. The method of claim 1, wherein the cuvette is configured as a single-use device and the probe is configured as a reusable device.

10. The method of claim 1, wherein the probe is configured to monitor properties of the blood passing through the central bore without contacting the blood.

11. A method of monitoring blood in an extracorporeal blood circuit, comprising:

directing venous blood through a central bore of a first cuvette positioned in a venous blood line of the extracorporeal blood circuit, the first cuvette comprising a first cuvette body defining a wall having an aperture extending therethrough and a sensor window formed separately from and thereafter disposed across the sensor window of the first cuvette body with an inner surface of the sensor window facing the central bore of the first cuvette, wherein the venous blood directed through the central bore of the first cuvette contacts the inner surface of the sensor window;

monitoring properties of venous blood passing through the central bore of the first cuvette via the sensor window of the first cuvette using a first probe disposed outside of the first cuvette;

directing arterial blood through a central bore of a second cuvette positioned in an arterial blood line of the extracorporeal blood circuit, the second cuvette comprising a sensor window disposed in a side wall of the second cuvette;

monitoring properties of arterial blood passing through the central bore of the second cuvette via the sensor window of the second cuvette using a second probe disposed outside of the second cuvette.

12. The method of claim 11, wherein the first probe comprises at least one of light emitting diodes (LEDs), an optical sensor, and an infrared sensor.

13. The method of claim 11, wherein the second probe comprises at least one of light emitting diodes (LEDs), an optical sensor, and an infrared sensor.

14. A method of monitoring blood in an extracorporeal blood circuit, comprising:

directing venous blood through a central bore of a first cuvette positioned in a venous blood line of the extracorporeal blood circuit, the first cuvette comprising a cylindrical body including a planar exterior surface configured to engage a first probe;

coupling the first probe to the first cuvette such that the first probe is juxtaposed with the planar exterior surface;

monitoring properties of venous blood passing through the central bore of the first cuvette using the first probe;

directing arterial blood through a central bore of a second cuvette positioned in an arterial blood line of the extracorporeal blood circuit, the second cuvette comprising a cuvette body defining a wall having an aperture extending therethrough and a sensor window formed separately from and thereafter disposed across the sensor window of the second cuvette body with an inner surface of the sensor window facing the central bore of the second cuvette, wherein the arterial blood directed through the central bore of the second cuvette directly contacts the inner surface of the sensor window;

coupling a second probe to the second cuvette such that the second probe is juxtaposed with the sensor window; and monitoring properties of arterial blood passing through the central bore of the second cuvette using the second probe.

15. The method of claim 14, wherein the sensor window is optically transmissive and the second probe includes an optical sensor.

16. The method of claim 15, wherein the sensor window comprises a fluorescent coating sensitive to blood oxygen partial pressures facing toward the central bore and in contact with the arterial blood.

17. The method of claim 14, wherein the first probe does not contact the venous blood.

18. The method of claim 14, wherein the second probe does not contact the arterial blood.

* * * * *